(12) United States Patent
Bäck

(10) Patent No.: US 10,531,993 B2
(45) Date of Patent: Jan. 14, 2020

(54) ABSORBENT ARTICLE

(71) Applicant: SCA HYGIENE PRODUCTS AB, Göteborg (SE)

(72) Inventor: Lucas Bäck, Billdall (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 54 days.

(21) Appl. No.: 15/537,771

(22) PCT Filed: Dec. 19, 2014

(86) PCT No.: PCT/SE2014/051549
§ 371 (c)(1),
(2) Date: Jun. 19, 2017

(87) PCT Pub. No.: WO2016/099362
PCT Pub. Date: Jun. 23, 2016

(65) Prior Publication Data
US 2018/0271715 A1    Sep. 27, 2018

(51) Int. Cl.
*A61F 13/15* (2006.01)
*A61F 13/496* (2006.01)
(Continued)

(52) U.S. Cl.
CPC ........ *A61F 13/496* (2013.01); *A61F 13/4942* (2013.01); *A61F 13/49061* (2013.01); *A61F 13/49466* (2013.01); *A61F 2013/4948* (2013.01)

(58) Field of Classification Search
CPC .............. A61F 13/496; A61F 13/49061; A61F 13/4942; A61F 13/49466; A61F 2013/4948
(Continued)

(56) References Cited

U.S. PATENT DOCUMENTS 3,766,922 A   10/1973  Krusko
5,032,120 A    7/1991  Freeland et al.
(Continued)

FOREIGN PATENT DOCUMENTS

CN      1 626 050 A     6/2005
CN      1 708 272 A    12/2005
(Continued)

OTHER PUBLICATIONS

Office Action (Notice of Reasons for Rejection) dated Aug. 27 2018, by the Japanese Patent Office in corresponding Japanese Patent Application No. 2017-532848, and an English Translation of the Office Action. (16 pages).
(Continued)

*Primary Examiner* — Jacqueline F Stephens
(74) *Attorney, Agent, or Firm* — Buchanan Ingersoll & Rooney PC

(57) ABSTRACT

A pant type disposable absorbent article including a front body panel, a back body panel positioned at a distance from said front body panel, and an absorbent member; the absorbent article having a longitudinal central axis X-X and a transverse central axis Y-Y; the front body panel being substantially rectangular, and having a waist edge, two side edges, and an inward edge including a crotch edge and leg opening edges on each side of the crotch edge, between the crotch edge and each side edge, the front body panel being at least partially elasticized, the back body panel having a waist edge, two side edges, a crotch edge, and leg opening edges on each side of the crotch edge, between the crotch edge and each side edge, wherein a distance from the crotch edge to the waist edge is greater than the length of the side edges.

17 Claims, 7 Drawing Sheets

(51) Int. Cl.
*A61F 13/49* (2006.01)
*A61F 13/494* (2006.01)

(58) Field of Classification Search
USPC ............ 604/385.28, 385.24, 385.25, 385.26,
604/385.27, 385.29, 385.3, 385.31
See application file for complete search history.

(56) References Cited

U.S. PATENT DOCUMENTS

| | | | |
|---|---|---|---|
| 5,601,544 A | 2/1997 | Glaug et al. | |
| 5,911,713 A | 6/1999 | Yamada et al. | |
| 6,500,162 B1 | 12/2002 | Freiburger et al. | |
| 6,613,955 B1 | 9/2003 | Lindsay et al. | |
| 6,682,515 B1* | 1/2004 | Mizutani | A61F 13/4753 604/385.27 |
| 8,754,286 B2 | 6/2014 | Bergstrom et al. | |
| 8,853,487 B2 | 10/2014 | Takeuchi et al. | |
| 10,226,389 B2 | 3/2019 | Back | |
| 2002/0133131 A1 | 9/2002 | Rangachari et al. | |
| 2003/0139719 A1 | 7/2003 | Nanaumi et al. | |
| 2004/0116886 A1 | 6/2004 | Van Gompel et al. | |
| 2004/0210205 A1 | 10/2004 | VanGompel et al. | |
| 2004/0243085 A1 | 12/2004 | Veith et al. | |
| 2004/0243086 A1 | 12/2004 | VanGompel et al. | |
| 2006/0030831 A1* | 2/2006 | Matsuda | A61F 13/15699 604/392 |
| 2007/0239131 A1 | 10/2007 | Hermansson et al. | |
| 2007/0293833 A1 | 12/2007 | Wennerback | |
| 2008/0262459 A1 | 10/2008 | Kamoto et al. | |
| 2008/0312631 A1 | 12/2008 | Okuda | |
| 2009/0036860 A1 | 2/2009 | Sugiyama et al. | |
| 2009/0076473 A1 | 3/2009 | Kasai et al. | |
| 2009/0326504 A1 | 12/2009 | Kaneda | |
| 2010/0063468 A1 | 3/2010 | Lehto et al. | |
| 2010/0114048 A1 | 5/2010 | Bishop et al. | |
| 2011/0066127 A1* | 3/2011 | Kuwano | A61F 13/49001 604/385.3 |
| 2011/0071488 A1 | 3/2011 | Kuwano et al. | |
| 2012/0215191 A1* | 8/2012 | Takino | A61F 13/49011 604/365 |
| 2012/0226254 A1 | 9/2012 | Takino | |
| 2012/0302985 A1 | 11/2012 | Mukai et al. | |
| 2013/0030402 A1 | 1/2013 | Arayama et al. | |
| 2013/0041340 A1 | 2/2013 | Kawakami et al. | |
| 2013/0046266 A1 | 2/2013 | Kawakami | |
| 2013/0079742 A1 | 3/2013 | Kuwano et al. | |
| 2013/0096528 A1 | 4/2013 | Hashino et al. | |
| 2013/0245588 A1 | 9/2013 | Mishima et al. | |
| 2013/0267924 A1 | 10/2013 | Mukai et al. | |
| 2014/0163509 A1 | 6/2014 | Gassner et al. | |
| 2015/0032072 A1 | 1/2015 | Hashimoto et al. | |
| 2015/0088087 A1 | 3/2015 | Kawakami | |
| 2015/0238368 A1 | 8/2015 | Mukai et al. | |
| 2016/0058625 A1 | 3/2016 | Morimoto | |
| 2016/0235595 A1 | 8/2016 | Ehrnsperger et al. | |

FOREIGN PATENT DOCUMENTS

| | | |
|---|---|---|
| CN | 1976666 A | 6/2007 |
| CN | 102202629 A | 9/2011 |
| EP | 1 569 588 B1 | 9/2005 |
| EP | EP 1 870 067 A1 | 12/2007 |
| EP | 2 022 453 A1 | 2/2009 |
| EP | 2 120 828 A1 | 11/2009 |
| EP | 2 258 329 A1 | 12/2010 |
| EP | 2 540 269 A1 | 1/2013 |
| EP | 2 589 359 A1 | 5/2013 |
| GB | 2 105 592 A | 3/1983 |
| JP | S 58-65003 A | 4/1983 |
| JP | H 10243960 A | 9/1998 |
| JP | 2003284743 A | 10/2003 |
| JP | 2005027839 A | 2/2005 |
| JP | 2008036198 A | 2/2008 |
| JP | 2008531178 A | 8/2008 |
| JP | 2008302138 A | 12/2008 |
| JP | 2009160129 A | 7/2009 |
| JP | 2009233161 A | 10/2009 |
| JP | 2011030791 A | 2/2011 |
| JP | 2012075566 A | 4/2012 |
| JP | 2013000304 A | 1/2013 |
| JP | 2013013580 A | 1/2013 |
| JP | 2014023949 A | 2/2014 |
| JP | 2014068981 A | 4/2014 |
| JP | 2014069002 A | 4/2014 |
| JP | 2014076233 A | 5/2014 |
| TW | 590006 U | 6/2004 |
| TW | 200427439 A | 12/2004 |
| TW | 200507813 A | 3/2005 |
| TW | 200706164 A | 2/2007 |
| TW | 200706165 A | 2/2007 |
| TW | 200726448 A | 7/2007 |
| TW | 201238573 A | 10/2012 |
| TW | 201315450 A | 4/2013 |
| TW | 201400100 A | 1/2014 |
| WO | WO 2004/1052260 A1 | 6/2004 |
| WO | WO 2006/093439 A1 | 9/2006 |
| WO | WO 2008/079061 A1 | 7/2008 |
| WO | 2012042908 A1 | 4/2012 |
| WO | WO 2013/1005423 A1 | 1/2013 |
| WO | 2013187264 A1 | 12/2013 |

OTHER PUBLICATIONS

Office Action (Reason's) dated Aug. 20, 2018, by the Japanese Patent Office in corresponding Japanese Patent Application No. 2017-532832, and an English Translation of the Office Action. (16 pages).

Office Action (Examination Report No. 1 for Standard Patent Application) dated May 29, 2017, by the Australian Patent Office in tile Australian Patent Application No. 2014414117. (3 pages).

Search Report issued by the Russian Patent Office in the Russian Application No. 2017125536. (2 Pages).

Notification of Transmittal of the International Search Report (Forms PCT/ISA/220 and PCT/ISA/210) and the Written Opinion of the International Searching Authority (Form PCT/ISA/237) dated Sep. 15, 2015, by the European Patent Office in the International Application No. PCT/SE2014/051550. (14 Pages)

Written Opinion of the International Preliminary Examining Authority (Form PCT/IPEA/408) dated Nov. 29, 2016, by the European Patent Office in the International Application No. PCT/SE2014/051550. (9 Pages).

Notification of Transmittal of the International Preliminary Report on Patentability (Forms PCT/IPEA/416 and PCT/IPEA/409) dated Feb. 14, 2017, by the European Patent Office in the International Application No. PCT/SE2014/051550. (11 Pages).

Office Action (Examination Report No. 1 for Standard Patent Application) dated May 29, 2017, by the Australian Patent Office in corresponding Australian Patent Application No. 2014414117. (3 pages).

Office Action (Examination Report No. 1 for Standard Patent Application) dated May 31, 2017, by the Australian Patent Office in the Australian Patent Application No. 2014414118. (3 pages)

Bäck, U.S. Appl. No. 15/537,815, entitled "Absorbent Article" filed Jun. 19, 2017.

International Search Report (PCT/ISA/210) dated Sep. 15, 2015, by the European Patent Office as the International Searching Authority for International Application No. PCT/SE2014/051549.

Written Opinion (PCT/ISA/237) dated Sep. 15, 2015, by the European Patent Office as the International Searching Authority for International Application No. PCT/SE2014/051549.

Written Opinion of the International Preliminary Examinating Authority (PCT/IPEA/408) dated Nov. 29, 2016, by the European Patent Office as the International Examining Authority for International Application No. PCT/SE2014/051549.

International Preliminary Report on Patentability (PCT/IPEA/409) dated Feb. 14, 2017, by the European Patent Office as the International Examining Authority for International Application No. PCT/SE2014/051549.

(56) References Cited

OTHER PUBLICATIONS

Office Action (Notice of Grounds for Preliminary Rejection) dated Oct. 22, 2018, by the Korean Intellectual Property Office in corresponding Korean Patent Application No. 10-2017-7019641, and an English Translation of the Office Action, (14 pages).
Office Action (Desicion of Rejection) dated Mar. 4, 2019, by the Japanese Patent Office in corresponding Japanese Patent Application No. 2017-532848, and an English Translation of the Office Action. (12 pages).
Office Action (Notice of Grounds for Preliminary Rejection) dated Oct. 19, 2018, by the Korean Patent Office in Korean Patent Application No. 10-2017-7019592, and an English translation of the Office Action. (13 pages).
Decision of Final Rejection dated Jul. 19, 2019, by the Korean Intellectual Property Office in corresponding Korean Patent Application No. 10-2017-7019641 and an English translation of the Office Action. (7 pages).
Official Action issued in corresponding Chinese Patent Application No. 201480084212.0, dated Oct. 9, 2019, with English translation (18 pages).

\* cited by examiner the back portion to the length L1 of the front portion is L2:L1<0.4, preferably <0.3, more preferably <0.25. Alternatively, the crotch, edge of the back body panel is located in front of the imaginary centre line. By means of this construction, the back panel is attached to the absorbent member with its crotch edge relatively far forward in the article, and the leg opening edges are located relatively low on the wearer's leg when in use. The back body panel will thereby cover the buttocks of the wearer to a great extent, giving wearer comfort and reduced leakage risk.

ABSORBENT ARTICLE

TECHNICAL FIELD

The present invention relates to a pant type disposable absorbent article.

BACKGROUND ART

Pant-type absorbent articles commonly include a pant-shaped chassis structure and an absorbent core component integrated with the chassis. A major objective when designing pant articles is to make them resemble ordinary underwear as closely as possible. Hence, absorbent articles such as pant diapers, sanitary pants and incontinence pants are designed to fit comfortably and snugly about the wearer. It is also desirable that the articles are capable of being pulled up and down over the hips of the wearer in the manner of a pair of underpants to allow the wearer or caregiver to easily remove a soiled article and to replace it with a new clean article. For these reasons, the article chassis is usually made of a material that is elastically stretchable around the waist and in the areas intended to be applied over the wearer's hips. An example of a pant type absorbent article is shown in EP2120828.

SUMMARY

The aim of the invention is to provide a pant type disposable absorbent article having, improved wearer comfort and reduced risk of leakage. The absorbent article comprises a front body panel, a back body panel positioned at a distance from said front body panel, and an absorbent member being attached to and bridging said front body panel and said back body panel, and has a longitudinal central axis X-X and a transverse central axis Y-Y. The front body panel is substantially rectangular, and has a waist edge, two side edges, and an inward edge comprising a crotch edge and leg opening edges on each side of the crotch edge, between the crotch edge and each side edge. The front body panel is at least partially elasticized. The back body panel has a waist edge, two side edges, a crotch edge, and leg opening edges on each side of the crotch edge, between the crotch edge and each side edge, wherein a distance from the crotch edge to the waist edge is greater than the length of the side edges. The back body panel is at least partially elasticized. The side edges of the front body panel are joined to the corresponding side edges of the back body panel.

The absorbent member has a substantially rectangular shape, and comprises a liquid permeable top sheet layer, an absorbent body and a liquid impermeable back sheet layer. The absorbent member further comprises a front attachment portion attached to the front body panel, a back attachment portion attached to the back body, panel, and an intermediate crotch portion extending from the crotch edge of the inward edge of the front body panel to the crotch edge of the back body panel.

An imaginary centre line coinciding with the transverse central axis Y-Y divides the absorbent article in two parts of, equal longitudinal length. The imaginary centre line may divide the intermediate crotch portion of the absorbent member into a front crotch portion located between the imaginary centre line and the crotch edge of the front body panel, and a back crotch portion between the imaginary centre line and the crotch edge of the back body panel, wherein the front portion has a length L1, and the back portion has a length L2, wherein the ratio of the length L2 of the back portion to the length L1 of the front portion is L2:L1<0.4, preferably <0.3, more preferably <0.25. Alternatively, the crotch, edge of the back body panel is located in front of the imaginary centre line. By means of this construction, the back panel is attached to the absorbent member with its crotch edge relatively far forward in the article, and the leg opening edges are located relatively low on the wearer's leg when in use. The back body panel will thereby cover the buttocks of the wearer to a great extent, giving wearer comfort and reduced leakage risk.

The absorbent body has a total length L3, the front attachment portion has a length L4, the back attachment portion has a length L5, and the intermediate crotch portion has a length L6, said lengths being taken in the longitudinal direction of the absorbent article. Preferably, the ratio of the length L6 of the intermediate crotch portion to the length L3 of the absorbent body is L6:L3=1:2.4 to 1:3.5, preferably 1:2.5 to 1:3; and the ratio of the length 14 of the front attachment portion to the length L5 of said back attachment portion is L4:L5=1:1.4 to 1:2.5, preferably 1:1.6 to 1:2.3, most preferably 1:1.8 to 1:2.2. This further contributes to the fit of the article to the wearer's body.

Front leg elastics may be arranged on each leg opening edge of the front body panel, and back leg elastics may be arranged on each leg opening edge of the back body panel. The absorbent member preferably comprises leg elastics on each side of the intermediate crotch portion, said leg elastics being the form of one or more elastic threads. Side leakage barriers are advantageously arranged longitudinally on each side of the absorbent member outside the absorbent body, which side leakage barriers extend along substantially the entire length of the absorbent member, and comprise elastics at a distal edge thereof.

The absorbent member may comprise an edge covering piece in the intermediate crotch portion, which edge covering piece is in the form of a separate piece of sheet material, which is attached to the garment side of the back sheet along an attachment line, and wrapped around the longitudinal edges of the back sheet and top sheet, and attached to the body facing side of the top sheet inward of the leg elastics. The edge covering piece may be tightly wrapped around the longitudinal edges of the back sheet and top sheet in such a way that substantially no excessive sheet material is present outside of the outermost elastic thread. In addition, the edge covering piece may extend further inwards from the attachment line on the top sheet, whereby the side leakage barriers are formed integrally with the edge covering piece.

The elastics of the side leakage barriers may have a first retraction force F1, and the leg elastics on the intermediate crotch portion may have a second retraction force F2, where the second retraction force is greater than the first retraction force.

Further, the back body panel may have an elasticity gradient, where the retraction force of the back body panel decreases in a direction from the waist edge towards the crotch edge.

When the above article is intended for use as an incontinence guard, wherein the length L5 of the back attachment portion of the absorbent member is 60-130 mm greater than the length L4 of the front attachment portion of the absorbent member.

When the above article is intended for use as a baby diaper, wherein the length L5 of the back attachment portion of the absorbent member is 40-80 mm greater than the length L4 of the front attachment portion of the absorbent member.

DETAILED DESCRIPTION

Figure 1:
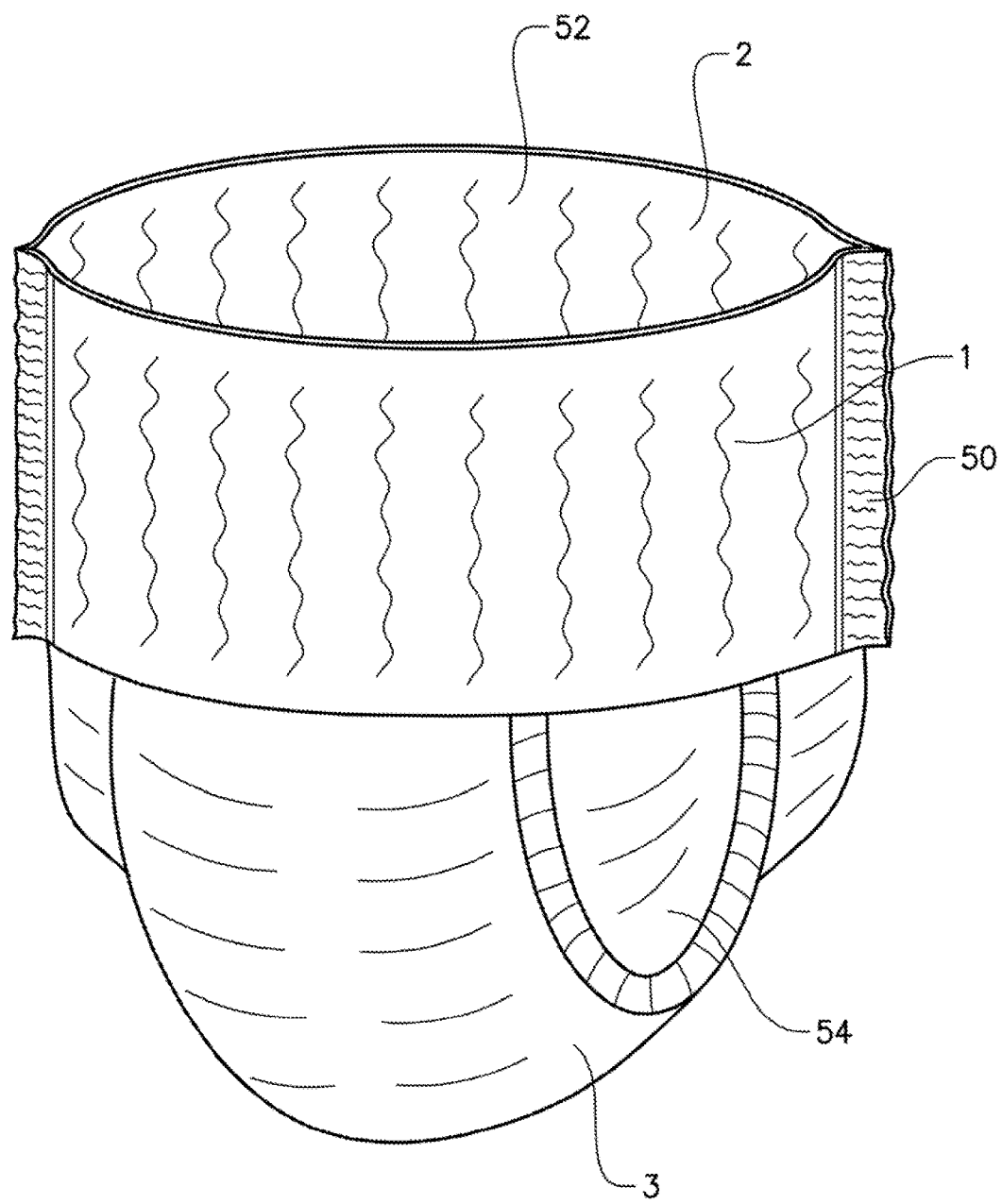
FIG. 1 is a schematic view of pant type absorbent article.

The pant type disposable absorbent article comprises a front body panel, a back body panel positioned at a distance from said front body panel, and an absorbent member being attached to and bridging said front body panel and, said back body panel. The article is comprised of the three separate main components which are joined to form a pant-like absorbent article, which can be worn similarly as an undergarment. By disposable is meant that the article is intended for single or temporary use, and to be discarded when soiled.

The front body panel is substantially rectangular, and has a waist edge, two side edges, and an inward edge comprising a crotch edge and leg opening edges on each side of the crotch edge, between the crotch edge and each side edge. The crotch edge may be substantially parallel to the waist edge, or may be slightly curved. The crotch edge and leg opening edges may typically be formed by portions of the inward edge, located side by side with the crotch edge portion between the leg opening portions. By substantially rectangular is mean that the front body panel can be rectangular, so that all of the crotch edge and leg opening edges are on the same distance from the waist edge, or that it can deviate slightly from a rectangular, for example so that the distance of the crotch edge from the waist edge is somewhat larger than the length of the side edges, and the leg opening edges are inclined in relation to the crotch edge. The leg opening edges may also be slightly curved.

The back body panel has a waist edge, two side edges, a crotch edge, and leg opening edges on each side of the crotch edge, between the crotch edge and each side edge. The distance from the crotch edge to the waist edge is greater than the length of the side edges. The crotch edge may be substantially parallel, to the waist edge, or may be slightly curved.

The pant-type absorbent article is formed with seams or joins at the side edges of the chassis structure to connect the front panel to the back panel, and to form a pant having a waist opening and leg openings. The side joins may be arranged so that they will be placed at the user's hips during use of the absorbent pants, but the seams could also be arranged more to the front of the article. The side-seams are preferably made such that they will provide sufficient integrity to the chassis while it is being put on and while it is being worn. This meal s that the side-seams should withstand the tensile stress arising when the pant-type article is pulled up over the wearer's hips and also, any stress that may occur at the side seams as a result of the wearer's movements during use of the article. However, it may be advantageous if the side-seams can be broken apart in a controlled manner after use of the article so that a soiled article can be easily removed from the user without having to be pulled down along the legs. The side-seams may be formed by welding techniques such as ultrasonic welding or thermo-welding of thermoplastic components in the chassis material, or by means of adhesive. The side edges of the back body panel preferably have at least the same length as the side edges of the front body panel.

The front body panel and the back body panel can be made of a nonwoven material or breathable film material, such as a perforated film, and the material may also be liquid permeable. The material of the front and back body panels may be a single layer, or a laminate comprising two or more layers of the same or different materials.

Elastics can be included in various locations of the article. Elasticity can be expressed as retraction force, which is the force with which the elastics retract when extended to a certain length. When evaluating a ratio of the elasticity between different components, it is not important which method is used, as long as it is the same for all components.

One example of a method for measuring retraction force is described below

Method of Determining the Retraction Force of Elastic Elements in Leg Elastic Members and Inner Side Leakage Barriers Definition Retraction force P(X) is the elastic force of a sample, which has been stretched so that X % of the maximum available extension remains. For example, P(30) is the retraction force obtained when a sample is stretched to 70% of the maximum available extension.

Equipment
  Absorbent articles to be tested
  Tensile test apparatus with a moving cylinder travelling at a constant speed of 500 mm/min and 20 N load cell.
  Equipment for stretching the absorbent article to determine the maximum available extension, such as tape, paper clips, magnets or the like.
  Marker pen and scissors
  Stopwatch
  Ruler with mm scale
  Flexible ruler with mm scale. Flexible curve rulers can be purchased from e.g. scalerulers.com, or www.mattonbutiken.se
  Test protocol Preparation of Samples for Determining Retraction Force
A) If the absorbent article is a pant article, then start to open up the sides, gently breaking the side joins.
B) To determine the maximum available extension of a leg elastic element and/or an inner side leakage barrier elastic element, the absorbent article is stretched and its corners are anchored to a flat surface. The absorbent article should thereby be stretched so that the materials surrounding the leg openings and the inner side leakage barrier elastic members are substantially flattened, i.e. substantially free from creases. The absorbent article should not be stretched to such an extent that the liquid-permeable top sheet layer or back sheet layer becomes overstretched, but should only be stretched until they are substantially free from crease. The anchoring of the absorbent article corners in the extended state is preferably carried out with tape, paper clips, magnets or the like.
C) A section having a length of 200 mm±2 mm is marked up on the extended leg elastic elements and on the extended inner side leakage barrier elastic elements. In case the elastic elements do not exhibit an extended length that allows marking of a 200 mm length, a section having a length of 100 mm±1 mm can be chosen instead.

The marked up sections should be substantially centered on the midpoints of the elastic members in a longitudinal direction.

If the leg, elastic elements or the side leakage barrier elastic element extend exhibit a curved extension, the section having a length of 200 mm±2 mm (or 100 mm±1 mm) is measured by means of a flexible ruler, whereby the flexible ruler is formed along the curved elastic element, followed by marking up a section of 200 mm±2 mm (or 100 mm±1 mm).

D) In order to determine the retraction force of the leg elastic elements, lines are marked up, which are parallel to the elastic elements at a distance of 5 mm±1 mm from the outermost and innermost arranged elastic elements, outside and inside thereof, respectively.

Sample strips are then cut out along the marked lines. Each strip includes all the elements located at the leg opening. The strips should be cut as long as possible, preferably along the entire length of the absorbent article.

In case there is less than 5 mm of material outside of the outermost elastic element on the leg opening, no line is marked and no material is cut off. This is noted in the test protocol.

In case the innermost elastic element on the leg opening is located less than 5 m from the longitudinal edge of the absorbent body no line is marked. The sample strip is then cut as close as possible to the absorbent body along the longitudinal edge thereof. This is noted in the test protocol. The sample strip separated from the absorbent article should be left completely free of extension for at least 30 minutes.

In order to determine the retraction force of the inner side leakage barrier elastic elements, a first line is marked parallel to the elastic members at a distance of 5 mm±1 mm from the outermost elastic element in the direction of the free edge of the inner side leakage barrier. By outermost elastic element is meant the elastic element which is arranged closest to the free edge of the inner side leakage barrier. In case the distance between the outermost elastic element and the free edge is less than 5 mm, no first line is marked. This is noted in the test protocol.

A second line is marked parallel with the elastic elements at a distance of 5 mm±1 mm rom the innermost elastic element in a direction towards the inner side leakage barrier connection to the liquid-permeable top sheet layer, i.e. the proximal edge of the inner side leakage barrier. By innermost elastic element is meant the elastic element which is arranged closest to the top sheet layer. In case the distance between the innermost elastic element and the liquid-permeable top sheet layer is less than 5 mm, no second line is marked. This is noted in the test protocol.

Sample strips are cut out along the marked first and second lines, each strip including all the elastic elements. If no first line as above is marked, no material is cut away, and if no second line is marked, the strip is cut as closely as possible to the liquid-permeable top sheet layer. The strips should be cut as long as possible, preferably along the entire length of the absorbent article. The sample strip separated from the absorbent article should be left completely free of extension for at least 30 minutes, Test The test is described herein for an elastic element, whet stretched so that 30% of the maximum available extension remains. When a retraction force P(30) is to be determined, the cut strips are placed in the tensile testing apparatus and stretched to 70% of the maximum available extension (280±2 mm or 100±1 mm), i.e. until the distance between-made markings is 140 mm (70 mm if the markings were made at a distance of 100 mm±1 mm) 30% of the maximum available extension means that 30% of the maximum available extension remains, hence the term P(30). The retraction force P(30) of the sample is noted within 5 seconds after completion of the stretching in order to obtain a complete test result for the leg opening elastic elements, elastic elements of both right and left leg openings of three absorbent articles should be tested. P(30) for the leg opening elastic elements is the mean value for the six tested elements.

In order to obtain a complete test result for the inner side leakage barrier elastic elements, elastic elements of both right and left inner side leakage barriers of three absorbent articles should be tested, P(30) for the inner side leakage barrier elastic elements is the mean value for the six tested elements.

If it is only possible to determine the P(30) value on 100±1 mm samples for one of the leg opening elastic element or the inner side leakage barrier elastic element, and on 200±2 samples on the other element, then the P(30) value measured on the 100±1 mm samples shall be used and the P(30) value measured on the 200±2 samples shall be used.

Both the front body panel and the back body panel are at least partially elasticized, in order to allow convenient dressing an undressing of the article. The elastics can be obtained by attaching a plurality of substantially parallel elastic threads on the web forming the front and back panels, and the distance between the threads can be chosen so as to obtain a desired fit around the hips of the wearer. For example, the elastic threads can be closer to each other in the area of the waist edge, than in the area substantially covering parts of the stomach and back of the wearer, between the waist edge and the crotch edge.

The front body panel may preferably comprise elastic threads distributed essentially over its entire surface in a direction parallel to the waist edge. The back body panel may have an elasticity gradient, where the retraction force of the back body panel decreases in a direction from the waist edge towards the crotch edge, in order to allow for an improved fit around the wearer's body. Such an elasticity gradient may be obtained by the back body panel comprising a plurality of areas of different elasticity, i.e. having different retraction force. For example, a first elastic area having a first retraction force may be located adjacent to the waist edge, and a second elastic area having a second retraction force, which is lower than the first retraction force, may be located adjacent to the first elastic area having in a direction towards the crotch edge. A third elastic area having a third retraction force, which is lower than the second retraction force, may be located adjacent to the second elastic area. Further, the back body panel may comprise a fourth area closest to the crotch edge, which fourth area is substantially non-elastic. The combined length in the longitudinal direction of the above mentioned first to third areas is preferably essentially the same as the length of the side seams joining the front and back body panels. In the first to third elastic areas, the desired retraction force can be obtained by elastic threads evenly distributed within each area, with the threads on a greater distance from each other in each area as compared to the adjacent preceding area in the direction toward the waist edge. Alternatively, the back body panel can comprise an elastic area with a continuously decreasing retraction force from the waist edge towards the crotch edge, said area ending approximately at, a line between the points where the leg opening edges meet the side seams. The continuously decreasing elasticity can be obtained by continuously increasing distance between elastic threads attached to the back body panel. Alternatively, an elastic web material, such as elastic nonwoven or elastic film, or a laminate including elastic web material, can be used for the front and back body panels. Elastic webs or laminates can also be combined with elastic threads.

The absorbent member has a substantially rectangular shape, and is produced as a separate component or "core pack" that has been integrated in the absorbent article by attachment to the front body panel and back body panel. The absorbent member comprises a liquid permeable top sheet layer, an absorbent body and a liquid impermeable back sheet layer. The longitudinal length of the absorbent body is typically slightly smaller than the longitudinal lengths of the top sheet and back sheet included in the absorbent member. The absorbent body may be substantially rectangular, or may be shaped so that it is narrower in the crotch region than at its end. The liquid-permeable top sheet layer can consist of any material known for the purpose, such as a layer of nonwoven material, a perforated plastic film, net material, tow, or the like. The top sheet can also consist of a laminate of two or more sheets of the same or different material. The liquid-impermeable back sheet layer can consist of a liquid-impermeable plastic film, a nonwoven sheet which has been coated with a liquid barrier material, or some other flexible material sheet which has the ability to withstand liquid penetration. However, it can be advantageous if the liquid-impermeable back sheet layer is breathable, i.e. permits the passage of water vapour through the back sheet.

The absorption body can be made up of absorbent material, such as cellulose fluff pulp, tissue, absorbent foam, etc. It is also possible for the absorption core to contain superabsorbents, i.e. polymer materials which are able to absorb body fluid corresponding to many times their own weight and form a hydrogel. Such superabsorbents are usually present in the form of particles, but fibres, flakes, granules and films are also available. Moreover, the absorption body can comprise non-absorbent components such as stiffening elements, shaping elements, binders, etc. The absorbent body may for example include absorbent material in the form of an embossed layer comprising cellulose pulp and superabsorbent particles. The embossed layer may comprise embossed areas forming an embossing pattern substantially uniformly distributed over the layer of absorbent material. The embossed areas cover 5-15%, and more preferably 7-13% of the surface of the layer of absorbent material, and contribute to the integrity of the layer of absorbent material. The layer of absorbent material comprised in the absorbent body may suitably have a density of 0.092-0.160 g/cm$^3$ and a basis weight 480-640 g/m$^7$. The absorbent material suitably has a density in the embossed areas, which is 028-0.62 g/cm$^3$.

If desired, the absorbent body may also comprise two folding lines arranged in the longitudinal direction in the layer of absorbent material comprised in the absorbent body of the absorbent member, in order to contribute to a bowl shape form of the absorbent member in the crotch portion. The folding lines can be arranged in parallel, and can be in the form of straight lines, or slightly arcuate lines. Preferably, such folding lines would extend along 10-50 of the length L3 of the absorbent body. For example, the folding lines may be embossed lines, in which the absorbent material is compressed to a lower thickness than an overall thickness of the layer of absorbent material. The density in the area of the folding lines is then preferably equal to, or higher than, the density in the embossed areas of the embossing pattern. Alternatively, the folding lines may be in the form of cuts or longitudinal openings in the layer of absorbent material, having a width in the transverse direction of 0-7 mm.

The absorbent body may be enclosed in a layer of liquid permeable tissue, in order to keep fibre fragments, SAP particles or the like within the absorbent body. The absorbent member can of course contain further components in addition to those described herein. Certain acquisition structures may be used on top of the absorbent body.

The absorbent member further comprises a front attachment portion attached to the front body panel, a back attachment portion attached to the back body panel, and an intermediate crotch portion extending from the crotch edge of the inward edge of the front body panel to the crotch edge of the back body panel.

The various components included in the absorbent member can be connected to one another in a conventional manner, for example by adhesive bonding, ultrasonic welding or thereto welding.

The absorbent article has a longitudinal central axis X-X and a transverse central axis Y-Y. An imaginary centre line coinciding with the transverse central axis Y-Y divides the absorbent article in two parts of equal longitudinal length. The imaginary centre line may divide the intermediate crotch portion of the absorbent member into a front crotch portion located between the imaginary centre lime and the crotch edge of the front body panel, and a back crotch portion between the imaginary centre line and the crotch edge of the back body panel, wherein the front portion has a length L1, and the back portion has a length L2, wherein the ratio of the length L2 of the back portion to the length L1 of the front portion is L2:L1<0.4, preferably <0.3, more preferably <0.25.

Alternatively, the crotch edge of the back body panel is located in front of the imaginary centre line. By means of this construction, the back body panel is attached to the absorbent member with its crotch edge relatively far forward in the article, and the leg opening edges are located relatively low on the wearer's leg when in use. The back body panel will thereby cover the buttocks of the wearer to a great extent, giving wearer comfort and reduced leakage risk.

The absorbent body of the absorbent member preferably has an elongated shape, and may suitably have a total length L3, which exceeds the longitudinal length of the crotch portion. The front attachment portion of the absorbent body has a length L4, the back attachment portion has a length L5, and the intermediate crotch portion has a length L6, said lengths being taken in the longitudinal direction of the absorbent article. The ratio of the length L6 of the intermediate crotch portion to the length L3 of the absorbent body is preferably L6:L3=1:2.4 to 1:3.5, preferably 1:2.5 to 1:3; and the ratio of the length L4 of the front attachment portion to the length L5 of said back attachment portion is L4:L5=1:1.4 to 1:2.5, preferably 1:1.6 to 1:2.3, most preferably 1:1.8 to 1:2.2. Thereby, an optimal positioning of the absorbent member is obtained which results in an optimal fit of the article.

In order to further improve the fit of the article, front leg elastics may be arranged on each leg opening edge of the front body panel, and back leg elastics may be arranged on each leg opening edge of the back body panel. The absorbent member may also comprise leg elastics on each side of the intermediate crotch portion. These leg elastics may for example be in the form of one or more elastic threads, or elastic bands. One or more elastic threads may be applied separately on each leg opening edge, whereby the length of the elastic threads is equal to or less than the length of the leg opening edge. Thereby the product seals against the thighs of the wearer and forms an additional leakage barrier for any liquid and/or faeces which may end up outside of the inner side leakage barrier. Alternatively, one or more elastic threads may be applied along the entire inward edge, of the front body panel, so that the same threads function as leg elastics on both front body panel leg opening edges. In this case, the elastic threads also run over the width of the absorbent member, and the threads may be applied in, a curve where they run over the absorbent member, so that they are farther away from the inward edge of the front body panel at the crotch edge portion, than at the leg opening portions. Such curve form elastics over the crotch edge portion may contribute to a bowl shape form in the crotch portion of the absorbent body.

Side leakage barriers may also be arranged longitudinally on each side of the absorbent member outside the absorbent body, so that they extend along substantially the entire length of the absorbent member, and elastics may suitably be comprised at a distal edge thereof. The elastics of the side leakage barriers may have a first retraction force F1, and the leg elastics on the intermediate crotch portion may have a second retraction force F2, the second retraction force being greater than the first retraction force. As said above, the retraction force is the force with which the elastics retract when extended to a certain length. The retraction forces F1 and F2 are suitably determined by means of the above described method. The retraction force P(30) for the elastics of the side leakage barriers corresponds to F1 and P(30) for the leg elastics on the intermediate crotch portion corresponds to F2. In the present context it is the relation between the elastics of the side leakage barriers and the leg elastics on the intermediate crotch portion that is relevant, which means that it is not important which method is used for determining the retraction forces. The retraction force of the elastics of the side leakage barriers, and the leg elastics on the intermediate crotch portion, refers to the retraction forces when the elastics is incorporated in the article, and thus refers to the retraction forces of the product elements side leakage barriers, and crotch portion edge, respectively, including elastic materials and any other layer included in the product element.

By means of the ratio of the retraction forces F1 and F2, the leg elastics contracts more that the side leakage barriers, which leads to an improved bowl shape in the crotch portion. This increases the ability of the absorbent article to temporary store a pool of liquid, which will subsequently be absorbed by the absorbent body.

The ratio of said first retraction force F1 to said second retraction force F2 is preferably F1:F2=1:1.2 to 1:2.8, preferably 1:15 to 1:2.5, more preferably 1:1.7 to 1:2.3. The leg elastics may have a higher retraction force during use since they are located adjacent to the thighs and groin area where they should provide tight fit and sealing against the skin. The side leakage barriers should also provide good sealing against the skin however, they may not have as high retraction force since they are typically having an inward orientation which makes them get in contact with sensitive genitals. The above given ratios have been found to be optimal for leg elastics providing tight fit around the thighs and leakage barriers providing more gentle sealing against the skin in the genital area.

The elastics of the side leakage barriers have a length L10, and the leg elastics on the intermediate crotch portion has a length L12, the ratio of the length L1 of the leg elastics (25) to the length L10 of the elastics (27) of the side leakage barriers is L12:L10=1:1.2 to 1:2, preferably 1:1.4 to 1:1.8.

The elastic material used for the elastics in the side leakage barriers and the crotch portion leg elastics may be the same or different. For example, elastic threads which per se have the same elasticity, i.e. the same retraction force can be used, and a larger number of elastic threads are then arranged in the leg elastics than in the standing gather elastics, for example three elastic threads in the leg elastics, and two elastic threads in the standing gather elastics.

Alternatively, elastic threads or bands, which per se have different elasticity can be used, or similar elastic threads or bands can be differently tensioned when attached.

The absorbent member may comprise an edge covering piece in the intermediate crotch portion, in the form of a separate piece of sheet material. The edge covering piece may then be attached to the garment side of the back sheet along an attachment line, and wrapped around the longitudinal edges of the back sheet and top sheet, and attached to the body facing side of the top sheet inward of the leg elastics. The edge covering piece may be for example a strip of nonwoven material or perforated film, and may be attached to the back sheet and top sheet by means of welding or gluing. Further, the edge covering piece may be tightly wrapped around the longitudinal edges of the back sheet and top sheet in such a way that substantially no excessive sheet material is present outside of the outermost elastic thread, so that the edge of the absorbent member can bear against the body of the wearer with a smooth edge border, further contributing to the fit and wearer comfort.

The edge covering piece may also extend further inwards from the attachment line on the top sheet, so that the side leakage barriers are formed integrally with the edge covering piece, thereby allowing for effective manufacture, since the number of separate parts is reduced. The pant type absorbent article may be used as an incontinence guard or a baby diaper. When the article is intended for use as an incontinence guard, wherein the length L5 of the back attachment portion of, the absorbent member may be 60-130 mm greater than the length L4 of the front attachment portion of the absorbent member. When the article is intended for use as a baby diaper, the length L5 of the back attachment portion of the absorbent member is 40-80 mm greater than the length L4 of the front attachment portion of the absorbent member.

The absorbent article will now be described by an example embodiment, reference to the drawings.

DESCRIPTION OF EXAMPLE EMBODIMENTS

The pant-type absorbent article will be described by reference to the drawings FIGS. 1-7, which show schematic views of different embodiments and details of the article. In the drawings, the same reference numeral is used for the same or corresponding detail or component.

FIG. 1 is a schematic view of a pant type absorbent article comprising a front body panel 1, a back body panel 2 and an absorbent member 3. The front and back body panels are joined to each other by means of side seams 50 at their corresponding side edges, so that a pant-like product is formed having a waist opening 52 and two leg openings 54.

Figure 2:
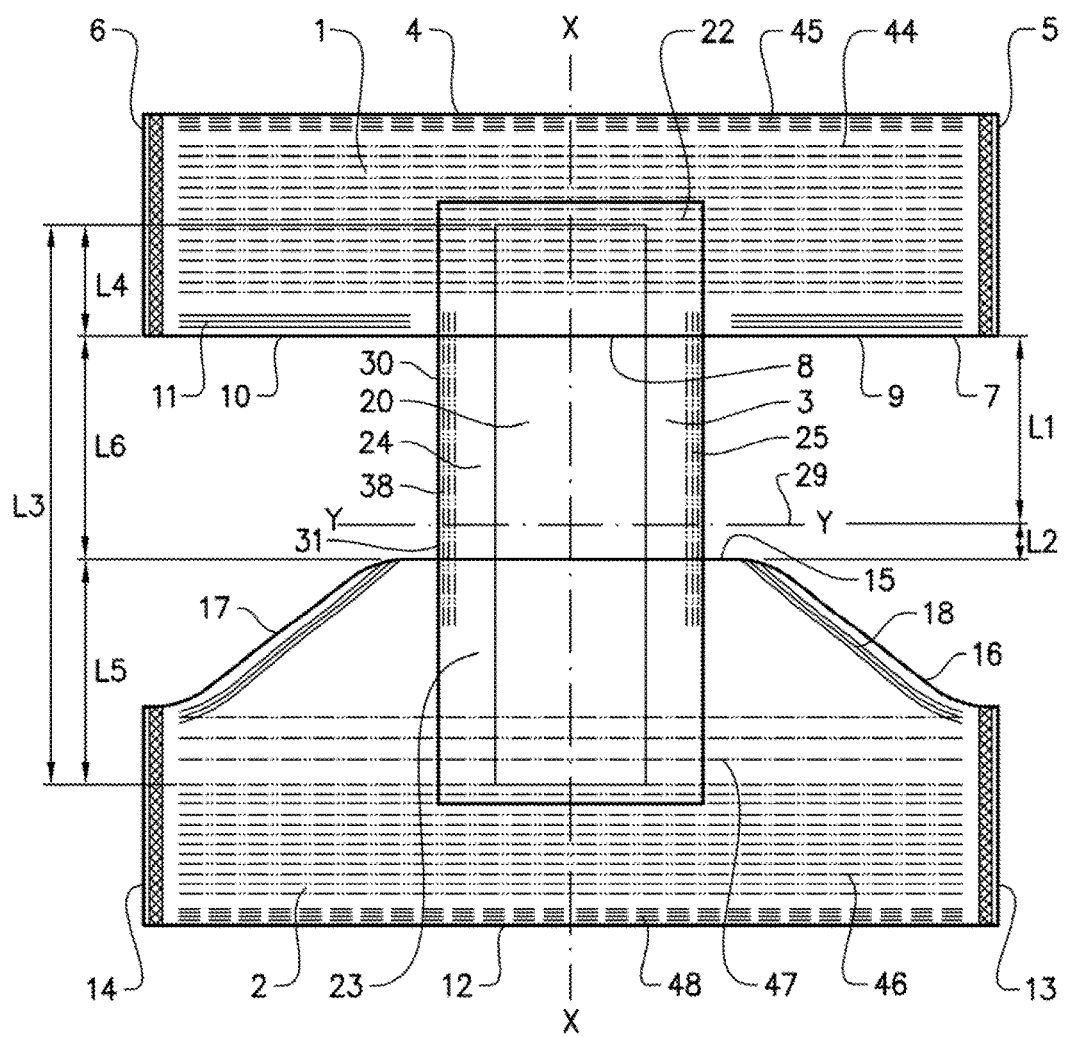
FIG. 2 is a schematic view of a first embodiment.

FIG. 2 is a schematic view of an absorbent article of a first embodiment, having a longitudinal central axis X-X and a transverse central axis Y-Y, shown before folding and joining the front and back body panels. The article comprises a front body panel 1, a back body panel 2 positioned at a distance from said front body panel, and an absorbent member 3, which is attached to and bridges the front body panel and said back body panel.

The front body panel 1 is substantially rectangular and has a waist edge 4, two side edges 5, 6, and an inward edge 7 comprising a crotch edge 8 and leg opening edges 9, 10 on each side of the crotch edge, between the crotch edge 8 and each side edge 9, 10. The front body panel is elasticized by means of elastic threads 44. Waist elastics 45 are applied adjacent to the waist edge 4.

The back body, panel 2 has a waist edge 12, two side edges 13, 14, a crotch edge 15 substantially parallel to the waist edge 12, and, leg opening edges 16, 17 on each side of the crotch edge, between the crotch edge 15 and each side edge 13, 14. The distance from the crotch edge 15 to the waist edge 12 is greater than the length of the side edges 13, 14. The back body panel is at least partially elasticized by means of elastic threads 46, 47. Waist elastics 48 are applied adjacent to the waist edge 12. The back body panel includes areas of different elasticity obtained by elastic threads applied at different distance from each other. As can be seen in FIG. 2 the elastic threads of the waist elastics are applied close to each other, followed by, in the direction of the crotch portion, two areas where the elastic threads are applied at increasingly greater distance from each other, followed by and closest to the crotch portion an area where no elastic threads are applied.

The side edges 5, 6 of the front body panel 1 are subsequently joined to the corresponding side edges 13, 14 of the back body panel 2 to form the pant-like article.

Figure 6:
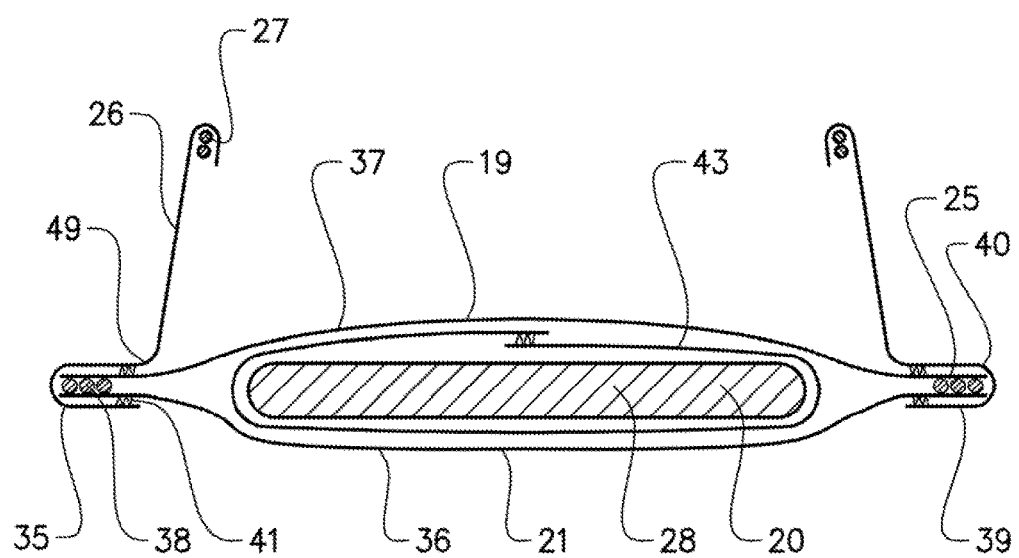
FIG. 6 is a schematic cross-sectional view of an absorbent member.

The absorbent member 3 has a substantially rectangular shape, and comprises a front attachment portion 22, a back attachment portion 23, and an intermediate crotch portion 24. The front attachment portion 22 is attached to the front body panel 1, and the back attachment portion 23 is attached to the back body panel 2. The intermediate crotch portion 24 extends from the crotch edge 8 of the inward edge of the front body panel 1 to the crotch edge 15 of the back body panel 2. As shown in FIG. 6, the absorbent member comprises a liquid permeable top sheet layer 19, an absorbent body 20 and a liquid impermeable, back sheet layer 21. Side leakage barriers 26 may be provided on the absorbent member, although this is not shown in FIGS. 1 to 4.

An imaginary centre line 29 coinciding with the transverse central axis Y-Y divides the absorbent article in two parts of equal longitudinal length. This imaginary centre line divides the intermediate crotch portion 24 of the absorbent member 3 into a front crotch portion 30 located between the imaginary centre line 29 and the crotch edge 8 of the front body panel 1, and a back crotch portion 31 between the imaginary centre line 29 and the crotch edge 15 of the back body panel 2. The front portion 30 has a length L1, and the back portion 31 has a length L2, and the ratio of the length L2 of the back portion to the length L1 of the front portion is L2:L1<0.4, preferably <0.3, more preferably <0.25.

The absorbent body 20 has a total length L3, the front attachment portion 22 has a length L4, the back attachment portion 23 has a length L5, and the intermediate crotch portion 24 has a length L6, said lengths being taken in the longitudinal direction X-X of the absorbent article. The ratio of the length 16 of the intermediate crotch portion 24 to the length L3 of the absorbent body 20 is L6:L3=1:2.4 to 1:3.5, preferably 1:2.5 to 1:3; and the ratio of the length L4 of the front attachment portion 22 to the length 15 of said back attachment portion 23 is L4:L5=1:1.4 to 1:2.5, preferably 1: 1.6 to 1:2.3, most preferably 1:1.8 to 1:2.2. As can be seen in FIG. 2, the absorbent body 20 is slightly shorter than the absorbent member.

Front leg elastics 11 are arranged on each leg opening edge 9, 10 of the front body panel 1, and back leg elastics 18 are arranged on each leg opening edge 16, 17 of the back body panel 2. The elastic threads on the respective leg opening edges 9, 10 are separate from each other. The absorbent member 3 comprises leg elastics 25 on each side of the intermediate crotch portion 24, in the form of one or more elastic threads 38.

Figure 3:
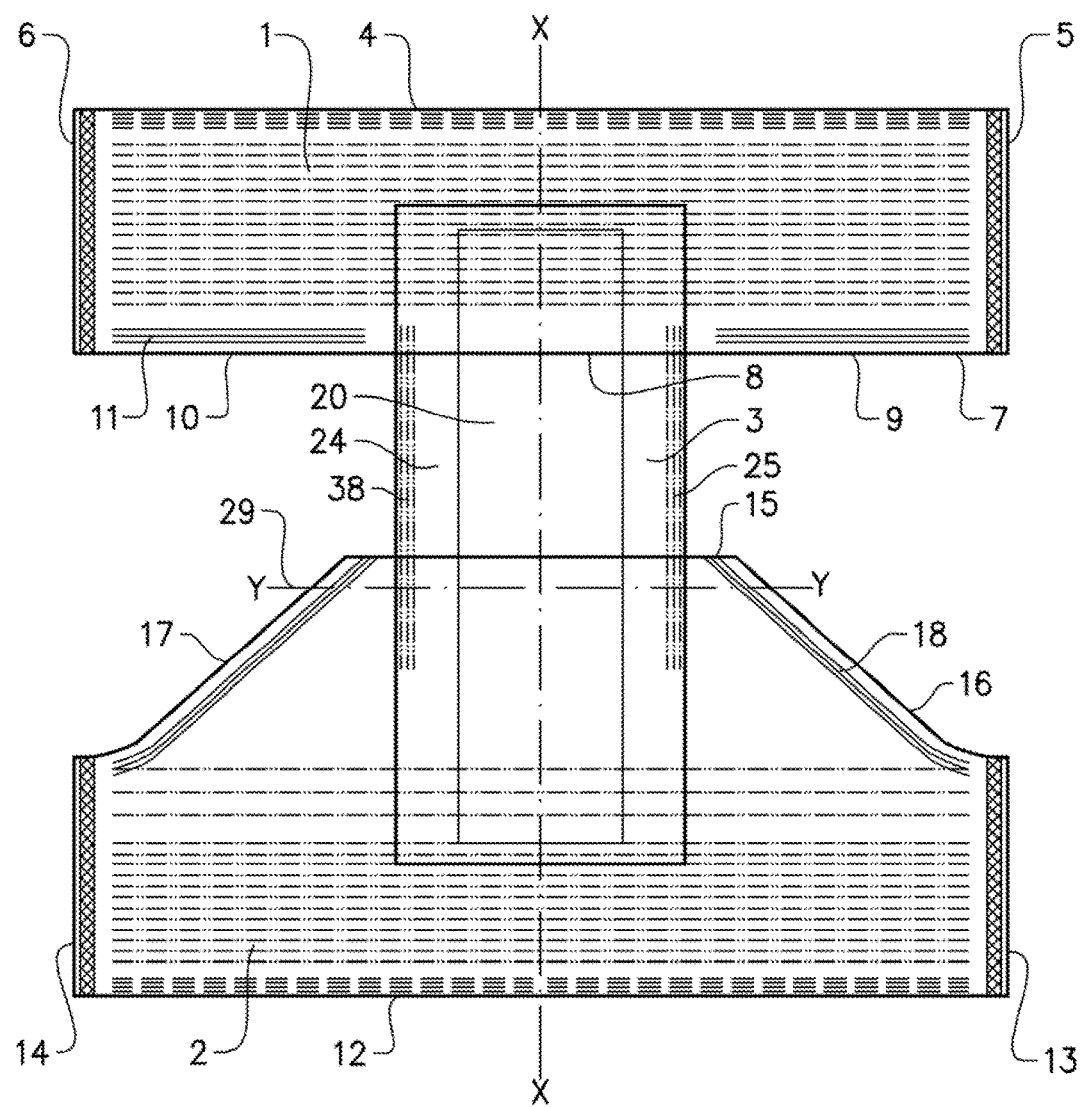
FIG. 3 is a schematic view of second embodiment.

FIG. 3 is a schematic view of an absorbent article of a second embodiment, shown before joining the front and back body panels, which is similar to the first embodiment, but wherein the crotch edge 15 of the back body panel 2 is located in front of the imaginary centre line 29.

Figure 4:
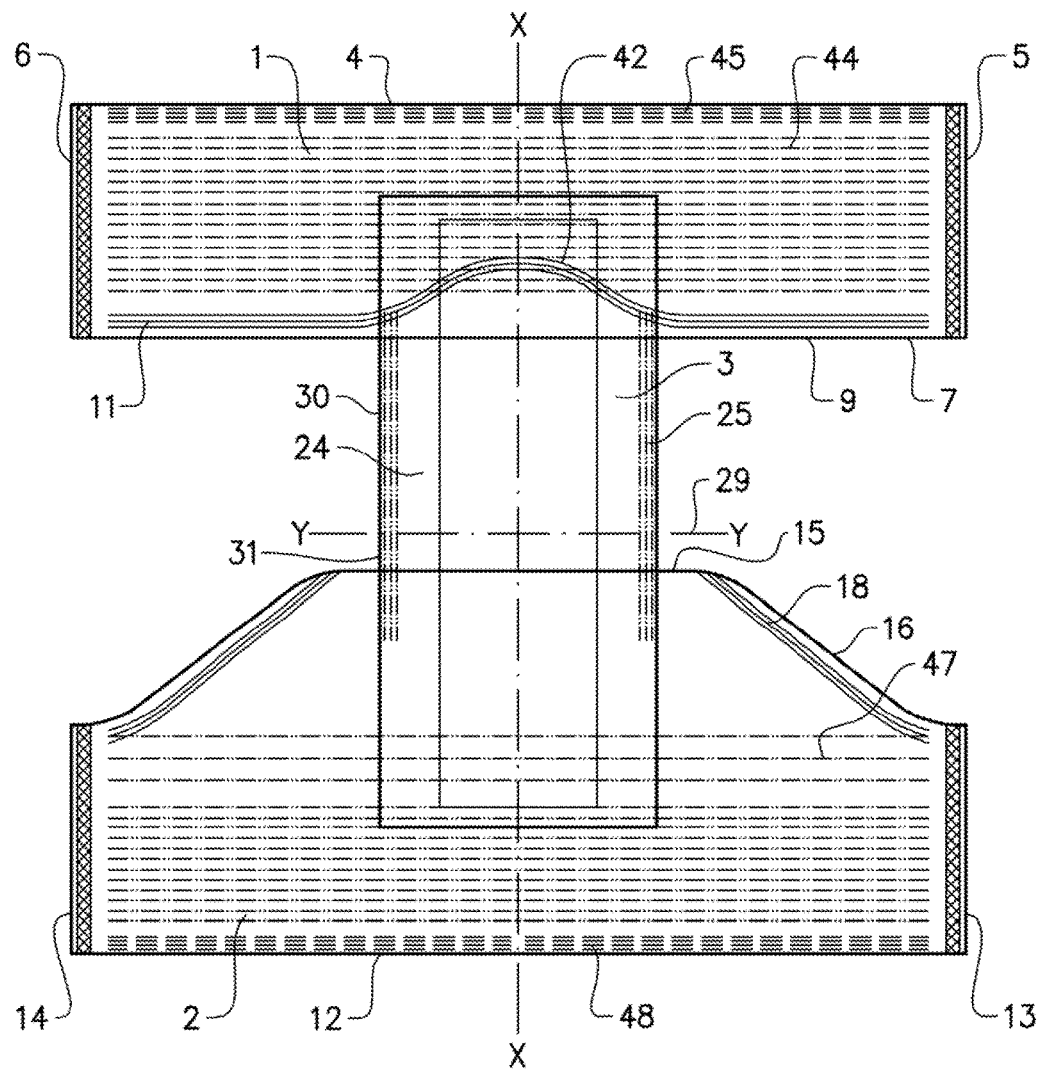
FIG. 4 is a schematic view of a third embodiment.

FIG. 4 is a schematic view of an absorbent article of a third embodiment, shown before joining the front and back body panels. In this embodiment, the elastic threads 11 of the leg opening elastics run across the absorbent member 3 so that the same threads are used for the leg elastics of both leg opening edges 9, 10. The threads are applied in a curve 42 in the area where they cross the absorbent member 3, but it is also possible to apply the threads along a straight line across the absorbent member.

Figure 5:
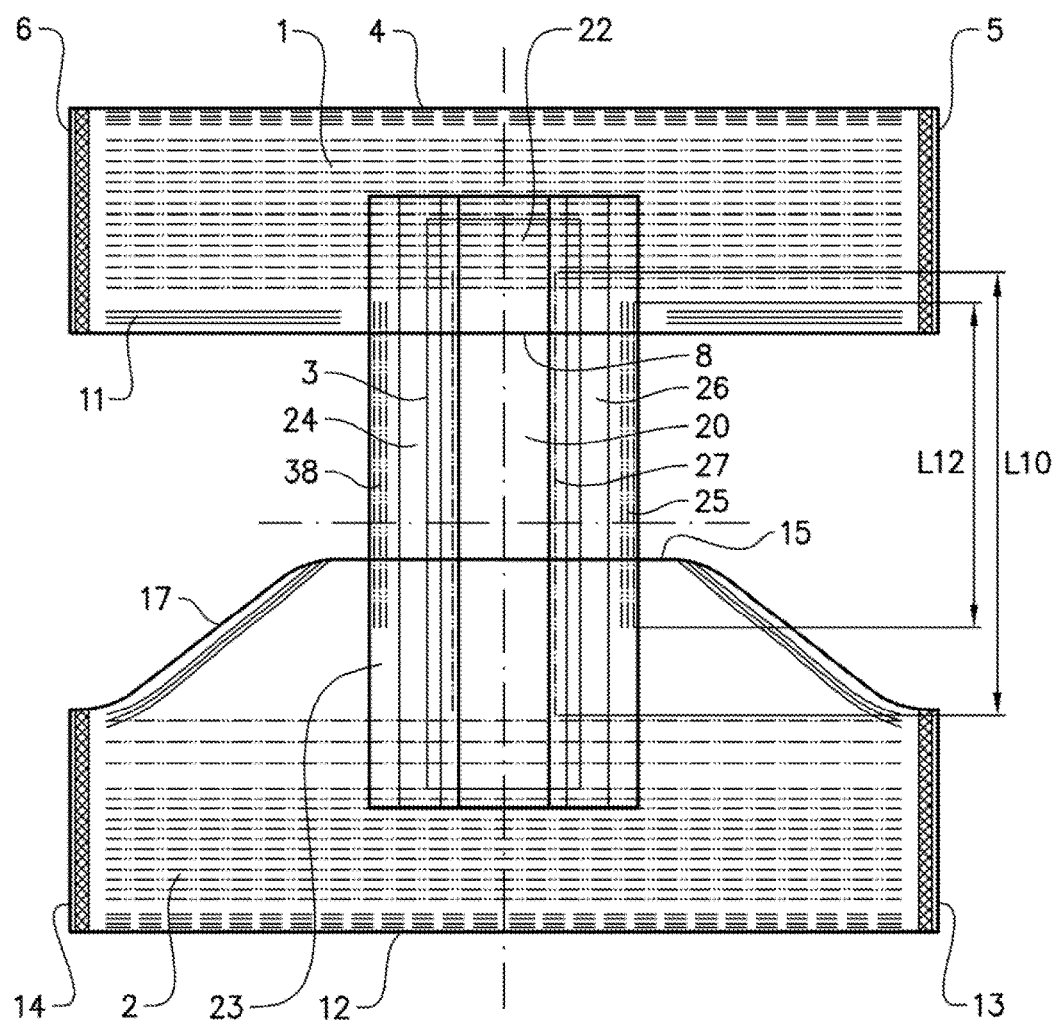
FIG. 5 is a schematic view of a fourth embodiment, similar to the embodiment, and further including side leakage barriers.

Side leakage barriers can be included in the articles of all embodiments. This is shown in FIG. 5, which is a schematic view of a fourth embodiment, similar to the first embodiment, and further including side leakage barriers. The side leakage barriers 26 are arranged longitudinally on each side of the absorbent member 3 outside the absorbent body 20, and extend along substantially the entire length of the absorbent member, and comprising elastics 27 at a distal edge thereof. The elastics 27 of the side leakage barriers 26 have a length 110 and the leg elastics 25 on the intermediate crotch portion 24 has a length 112, and the ratio of the length 112 of the leg elastics 25 to the length 110 of the elastics 27 of the side leakage barriers is suitably L12:L10=1:1.2 to 1:2, preferably 1:1.4 to 1:1.8.

FIG. 6 is a schematic cross-sectional view of an absorbent member of the embodiment in FIG. 5, taken along the imaginary centre line 29. However, the embodiments of FIGS. 2-4 also include an absorbent member of this type. The absorbent member comprises a liquid permeable top sheet layer 19, an absorbent body 20 and a liquid impermeable back sheet layer 21. The absorbent body 20 includes a layer of absorbent material 28, which is enclosed in an optional layer of tissue 43.

Side leakage barriers 26 are included and comprise elastics 27 at a distal edge thereof. The elastics 27 of the side leakage barriers 26 has a first retraction force F1, and the leg elastics 25 on the intermediate crotch portion 24 has a second retraction force F2, the second retraction force being greater than the first retraction force. The side leakage barriers may be omitted if desired.

FIG. 6, also illustrates how the absorbent member 3 comprises an edge covering piece 35 in the intermediate crotch portion 24. The edge covering piece 35 is in the form of a separate piece of sheet material, which is attached to the garment side 36 of the back sheet 21 along an attachment line 41, and wrapped around the longitudinal edges 39, 40 of the back sheet 21 and top sheet 19, and attached to the body facing side 37 of the top sheet inward of the elastic threads 38. The edge covering piece 35 is tightly wrapped around the longitudinal edges 39, 40 of the back sheet 21 and top sheet 19 in such a way that substantially no excessive sheet material is present outside of the outermost elastic thread.

The edge covering piece 35 extends further inwards from the attachment line 49 on the top sheet 19, so that the side leakage barriers 26 are, formed integrally with the edge covering piece 35. This edge covering piece can be applied in all, embodiments. The side leakage barriers 25 are attached in an inwardly oriented position in each end of the longitudinal ends of the absorbent member 3, Due to the tensioned elastics 27, the barriers are raised away from the top sheet 19 between the attachment areas in the ends of the barriers when the article is in use.

Figure 7:
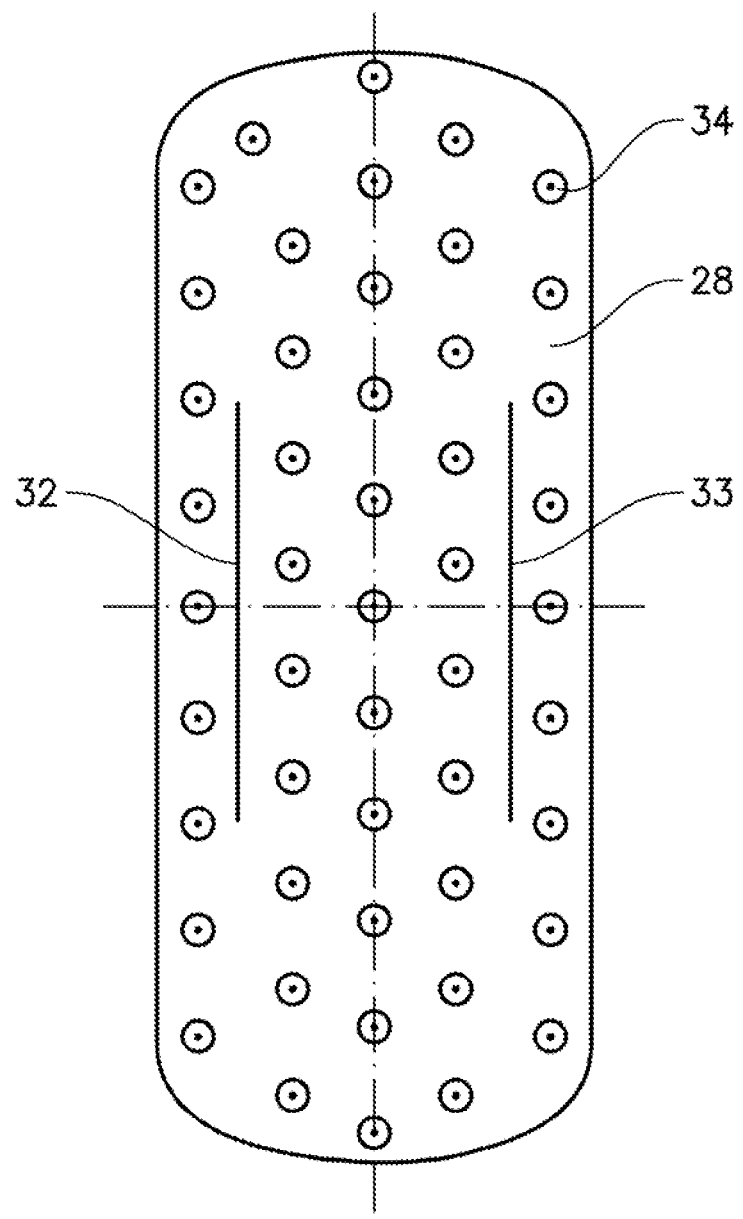
FIG. 7 is a schematic top view of an absorbent layer

FIG. 7 is a schematic top view of an absorbent layer 28, which is comprised in the absorbent body. The absorbent layer 28 is an embossed layer of absorbent material, and includes a pattern of embossed areas 34, and embossed or cut folding, lines 32, 33. This kind of absorbent layer can be used in all embodiments.

The invention claimed is:

1. A pant type disposable absorbent article comprising a front body panel, a back body panel positioned at a distance from said front body panel, and an absorbent member being attached to and bridging said front body panel and said back body panel; said absorbent article having a longitudinal central axis X-X and a transverse central axis Y-Y;
   said front body panel being substantially rectangular, and having a front waist edge, two front side edges, and an inward edge comprising a front crotch edge and leg opening edges on each side of the front crotch edge, between the front crotch edge and each side edge, said front body panel being at least partially elasticized,
   said back body panel having a rear waist edge, two back side edges, a back crotch edge, and leg opening edges on each side of the back crotch edge, between the back crotch edge and each of the back side edges,
   wherein the back crotch edge is a first distance from the rear waist edge,
   for each of the back side edges, a first end point of each of the back side edges is a second distance from a second end point, at an opposite end of each of the back side edges,
   wherein the first distance is greater than the second distance;
   said back body panel being at least partially elasticized;
   the front side edges of the front body panel being joined to the corresponding rear side edges of the back body panel;
   said absorbent member having a substantially rectangular shape, and comprising a liquid permeable top sheet layer, an absorbent body and a liquid impermeable back sheet layer; and comprising a front attachment portion being attached to the front body panel, a back attachment portion being attached to the back body panel, and an intermediate crotch portion extending from the front crotch edge of the inward edge of the front body panel to the back crotch edge of the back body panel;
   wherein the absorbent body has a total length L3, the front attachment portion has a length L4, the back attachment portion has a length L5, and the intermediate crotch portion has a length L6, said lengths L3, L4, L5, and L6 being taken in the longitudinal direction of the absorbent article; and
   the ratio of the length L6 of the intermediate crotch portion to the total length L3 of the absorbent body is L6:L3=1:2.4 to 1:3.5; and
   the ratio of the length L4 of the front attachment portion to the length L5 of said back attachment portion is L4:L5=1:1.4 to 1:2.5,
   wherein
   an imaginary centre line coinciding with the transverse central axis Y-Y divides the absorbent article in two parts of equal longitudinal length,
   wherein the imaginary centre line divides the intermediate crotch, portion of the absorbent member into a front crotch portion located between the imaginary centre line and the front crotch edge of the front body panel, and a back crotch portion between the imaginary centre line and the back crotch edge of the back body panel,
   wherein:
   the front portion has a length L1, and the back portion has a length L2, and wherein the ratio of the length L2 of the back portion to the length L1 of the front portion is L2:L1<0.4, or
   the back crotch edge of the back body panel is located in front of the imaginary centre line, and
   wherein back leg elastics are arranged along the leg opening edges on each side of the back crotch edge.

2. The absorbent article of claim 1, wherein front leg elastics are arranged on each leg opening edge of the front body panel.

3. The absorbent article of claim 1, wherein the absorbent member comprises leg elastics on each side of the intermediate crotch portion, said leg elastics being the form of one or more elastic threads.

4. The absorbent article of claim 3, wherein side leakage barriers are arranged longitudinally on each side of the absorbent member outside the absorbent body, said side leakage barriers extending along substantially the entire length of the absorbent member, and comprising elastics at a distal edge thereof.

5. The absorbent article of claim 3, wherein the elastics of the side leakage barriers has a first retraction force F1, and the leg elastics on the intermediate crotch portion has a second retraction force F2, the second retraction force being greater than the first retraction force.

6. The absorbent article of claim 3, wherein the absorbent member comprises an edge covering piece in the intermediate crotch portion, said edge covering piece being in the form of a separate piece of sheet material, which is attached to the garment side of the back sheet along an attachment line, and wrapped around the longitudinal edges of the back sheet and top sheet, and attached to the body facing side of the top sheet inward of the elastic threads.

7. The absorbent article of claim 6, wherein the edge covering piece is tightly wrapped around the longitudinal edges of the back sheet and top sheet in such, a way that substantially no excessive sheet material is present outside of the outermost elastic thread.

8. The absorbent article of claim 6, wherein said edge covering piece extends further inwards from the attachment line on the top sheet, whereby the side leakage barriers are formed integrally, with the edge covering piece.

9. The absorbent article of claim 8, wherein the back body panel has an elasticity gradient, where the retraction force of the back body panel decreases in a direction from the waist edge towards the crotch edge.

10. The absorbent article of claim 8, for use as an incontinence guard, wherein the length L5 of the back attachment portion of the absorbent member is 60-130 mm greater than the length L4 of the front attachment portion of the absorbent member.

11. The absorbent article of claim 8, for use as a baby diaper, wherein the length L5 of the back attachment portion of the absorbent member is 40-80 mm greater than the length L4 of the front attachment portion of the absorbent member.

12. The absorbent article of claim 8, wherein the ratio of the length L6 of the intermediate crotch portion to the length L3 of the absorbent body is L6:L3=1:15 to 1:3.

13. The absorbent article of claim 8, wherein the ratio of the length L4 of the front attachment portion to the length L5 of said back attachment portion is L4:L5=1:1.6 to 1:23.

14. The absorbent article of claim 8, wherein the ratio of the length L4 of the front attachment portion to the length L5 of said back attachment portion is L4:L5=1:1.8 to 1:2.2.

15. The absorbent article of claim 8, wherein the front crotch edge comprises the inward edge that is overlapping with the absorbent member, and the back crotch edge comprises an edge of the back body that overlaps with the absorbent member.

16. The absorbent article of claim 8, wherein the back leg elastics are continuous elastics.

17. The absorbent article of claim 8, wherein, in a transverse direction of the absorbent article, an entire area between the back leg elastics on each side of the back crotch edge is a non-elasticized area.

\* \* \* \* \*